(12) United States Patent
Pierce (10) Patent No.: US 7,058,456 B2
(45) Date of Patent: Jun. 6, 2006

(54) METHODS AND DEVICES FOR CHANGING THE SHAPE OF A MEDICAL DEVICE

(75) Inventor: Ryan Kendall Pierce, Mountain View, CA (US)

(73) Assignee: Concentric Medical, Inc., Mountain View, CA (US)

( * ) Notice: Subject to any disclaimer, the term of this patent is extended or adjusted under 35 U.S.C. 154(b) by 175 days.

(21) Appl. No.: 10/216,652

(22) Filed: Aug. 9, 2002

(65) Prior Publication Data

US 2004/0030375 A1    Feb. 12, 2004

(51) Int. Cl.
 *A61N 1/05* (2006.01)
(52) U.S. Cl. ...................................... 607/122
(58) Field of Classification Search ................ 606/159, 606/194, 195; 607/122
See application file for complete search history.

(56) References Cited

U.S. PATENT DOCUMENTS

| | | | |
|---|---|---|---|
| 3,868,956 A | 3/1975 | Alfidi et al. |
| 3,996,938 A | 12/1976 | Clark |
| 4,655,771 A | 4/1987 | Wallsten |
| 4,706,671 A | 11/1987 | Weinrib |
| 4,873,978 A | 10/1989 | Ginsburg |
| 4,969,891 A | 11/1990 | Gewertz |
| 4,994,069 A | 2/1991 | Ritchart et al. |
| 4,998,539 A | 3/1991 | Delsanti |
| 5,011,488 A | 4/1991 | Ginsburg |
| 5,054,501 A | 10/1991 | Chuttani et al. |
| 5,071,407 A | 12/1991 | Termin et al. |
| 5,256,146 A | 10/1993 | Ensminger |
| 5,514,176 A | 5/1996 | Bosley |
| 5,549,626 A | 8/1996 | Miller et al. |
| 5,562,698 A | 10/1996 | Parker |
| 5,688,234 A | 11/1997 | Frisbie |
| 5,702,413 A | 12/1997 | Lafontaine |
| 5,759,192 A * | 6/1998 | Saunders ..................... 606/194 |
| 5,895,398 A * | 4/1999 | Wensel et al. .............. 606/159 |
| 6,375,668 B1 | 4/2002 | Gifford et al. |
| 6,425,909 B1 | 7/2002 | Dieck et al. |
| 6,494,884 B1 | 12/2002 | Gifford et al. |
| 6,520,968 B1 | 2/2003 | Bates et al. |
| 6,592,607 B1 | 7/2003 | Palmer et al. |
| 6,652,536 B1 | 11/2003 | Mathews et al. |
| 6,663,650 B1 | 12/2003 | Sepetka et al. |
| 6,692,508 B1 | 2/2004 | Wensel et al. |
| 6,730,104 B1 | 5/2004 | Sepetka et al. |
| 6,824,545 B1 | 11/2004 | Sepetka et al. |

* cited by examiner

*Primary Examiner*—George Manuel
(74) *Attorney, Agent, or Firm*—Jens E. Hoekendijk (57) ABSTRACT

A medical device is movable between first and second positions. The medical device has an actuator which is movable between a relaxed position and a stacked position. The stacked position of the actuator deforms the medical device toward the stacked position of the actuator. When the actuator is in the relaxed position, the shape of the medical device is primarily determined by the shape of a main element.

19 Claims, 8 Drawing Sheets

METHODS AND DEVICES FOR CHANGING THE SHAPE OF A MEDICAL DEVICE

BACKGROUND OF THE INVENTION

The present invention is directed to medical devices and their methods of use. The present invention may find uses in various fields including, without limitation, cardiac, vascular, tracheobronchial, gastrointestinal, urological, or contraceptive medicine. For example, within cardiovascular applications the present invention may be used for removing obstructions from blood vessels, filtering blood flow, repairing vessels, and treating vasospasm or AVM's.

Numerous medical devices which are introduced into the body are expanded or deployed within the patient to perform a medical procedure. The present invention is directed to various methods and features associated with moving a medical device between two different positions or configurations.

SUMMARY OF THE INVENTION

The present invention provides a medical device having a main element and an actuating element. The main element is moved from a first position to a second position by the actuating element. The first position is defined by the geometry of the main element and may be linear, non-linear, helical, spiral, irregular, or the like. The first position and the second position will usually be different from one another and one position may be linear. Optionally, additional actuating element(s) could be included to provide additional position(s) for the device. In one aspect of the present invention, the actuating element is moved between stacked and relaxed positions. The actuating element moves from the relaxed position to the stacked position upon application of a compressive force to the actuating element. The main element moves from first position to second position as the actuating element moves from relaxed to stacked positions.

The actuating element may have a plurality of opposing surfaces longitudinally spaced along the main element. The plurality of opposing surfaces slide against one another when moving from the relaxed position to the stacked position. Once the stacked condition is formed, additional compressive force does not substantially change the stacked shape for many stable, stacked shapes. The geometries and relative positions of the opposing surfaces determine the shape of the actuating element in its stacked (actuated) configuration. That is, when the opposing surfaces are "stacked," they directly engage each other and displace each other in a manner defined by the shapes and/or orientations of the surfaces. The resulting engagement or interference causes the actuating element to assume the second position and overcome the natural shape of the main element and, within limits constraining forces resulting from the environment, such as a blood vessel or other body lumen. In one embodiment, the main element is a wire and the actuating element is also a wire which is wrapped around the main element. The actuating wire forms a stacked coil in the stacked position. The actuating wire may also have varying thickness to curve the main element in the stacked position. The actuating element may also be a tube, such as a hypotube, which is slotted or cut in a helical pattern.

The actuating element may also have a number of independent elements such as a number of rings which stack together in the stacked position. The main element may also have a non-circular cross-section which cooperates with the actuating elements to maintain the angular orientation of the actuating elements relative to the main element.

In another aspect of the present invention, a medical device is provided in which the main element is movable between expanded and collapsed positions. The main element is naturally biased toward the expanded position. The actuating element extends around the main element and is movable relative to the main element between a stacked position and a relaxed position. The main element is held in the collapsed position by the actuating element being in the compressed position.

In still another aspect of the present invention, a medical device is movable between a first shape and a second shape. The medical device has a first elongate member and a second elongate member. The second elongate member assumes a predefined shape when placed under compression. The first and second elongate members are coupled to one another so that the first member may be tensioned to compress the second member to cause the first and second elongate members to assume the predefined shape.

These and other aspects of the invention are described with reference to the description of the preferred embodiments described below. The examples presented below are intended to illustrate a few examples of medical devices which may be manufactured and/or used in accordance with any of the principles of the invention, however, it is understood that the present invention may have many other medical uses which are not described or mentioned here.

DETAILED DESCRIPTION OF PREFERRED EMBODIMENTS

Figure 1:
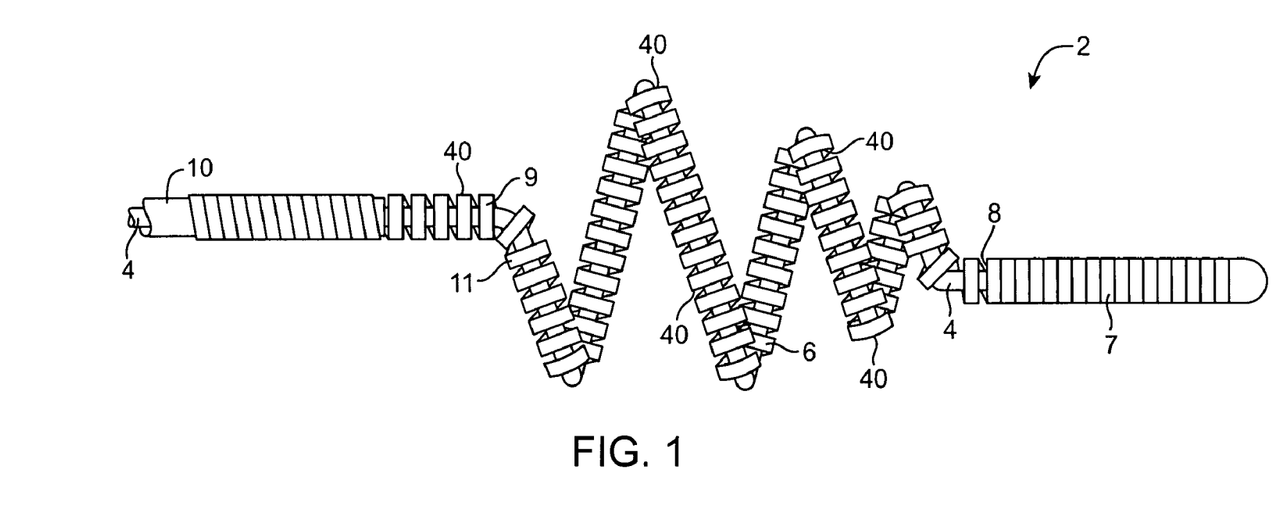
FIG. 1 shows a medical device in an expanded position.
Figure 4:
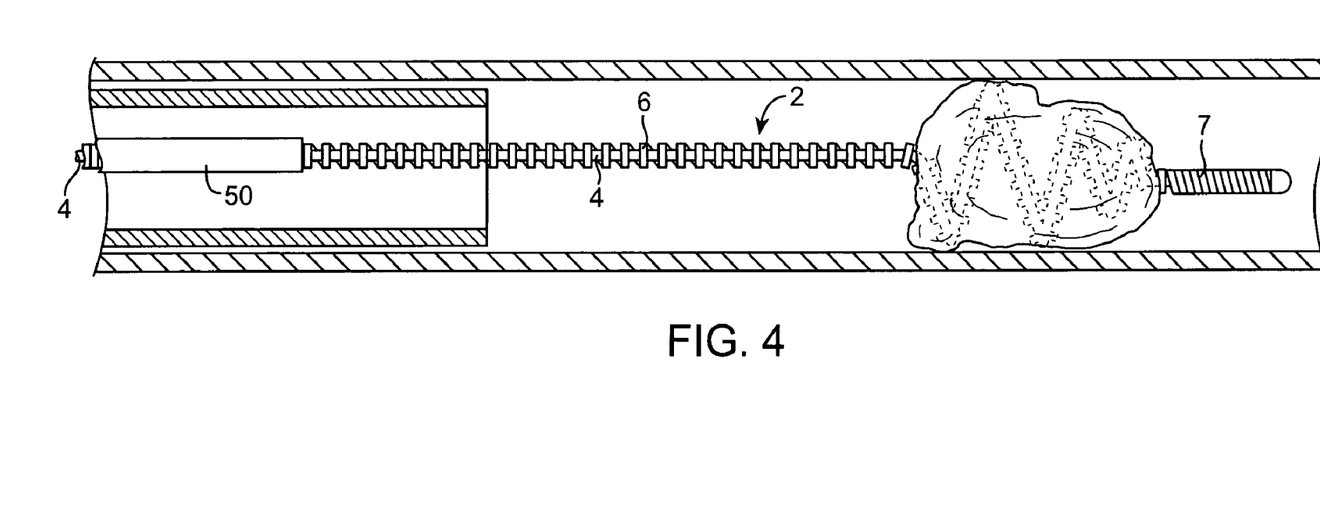
FIG. 4 shows the medical device expanded and in engagement with an obstruction.

Referring to FIGS. 1–4, a medical device 2 made in accordance with the present invention is shown. As mentioned above, various aspects of the present invention may be useful in a number of different medical devices and procedures. As an example of one such medical use, FIGS. 1–4 illustrate a device useful for removing thrombus, clots or other devices, such as embolic coils, which have migrated or formed in an undesirable location. The device 2 may be used to remove obstructions from a blood vessel in a manner similar to that described in U.S. Pat. No. 5,895,398 which is incorporated herein by reference. The device 2 is introduced into the patient in the collapsed shape of FIGS. 2 and 3 and is then expanded as shown in FIGS. 1 and 4 to engage the obstruction for removal from the patient.

The medical device 2 has a main element 4 and an actuating element 6. The main element 4 may be any suitable elongate element such as a wire, tube, filament or the like. For example, the main element 4 may be a wire 6 made out of a superelastic material or stainless steel. The main element 4 is naturally biased toward the expanded condition of FIG. 1 and is moved to the collapsed position of FIG. 2 with the actuating element 6. The actuating element 6 and main element 4 are attached to one another at an attachment point 8 using any suitable method such as soldering, mechanical interference, or adhesive. In one aspect of the invention, the main element 4 is attached to the actuating element 6 proximal to a distal portion 7 of the actuating element 6 to provide a soft tip. For example, the distal portion 7 may form a soft, helical coil at the distal portion 7. This feature is particularly advantageous when advancing the device 2 by itself through a blood vessel much like a guidewire is advanced through a blood vessel as described further below.

Figure 2:
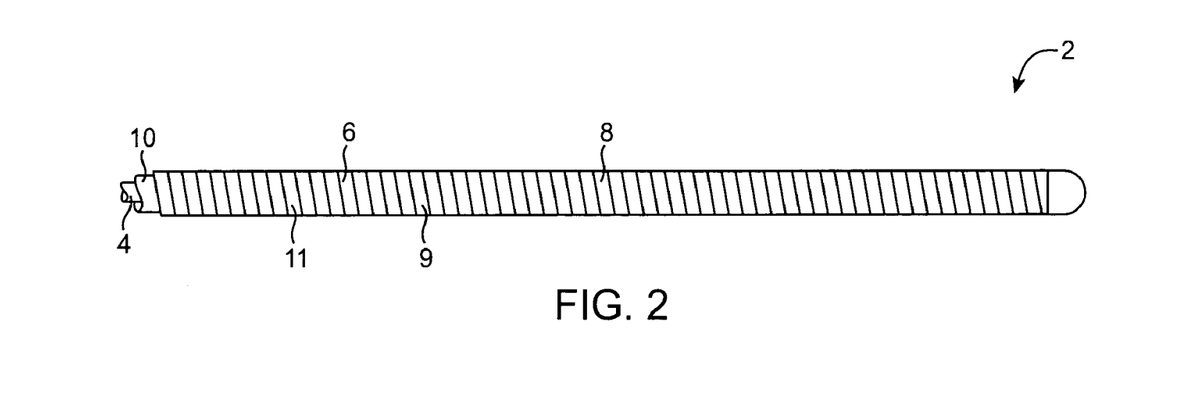
FIG. 2 shows the medical device in a collapsed position
Figure 3:
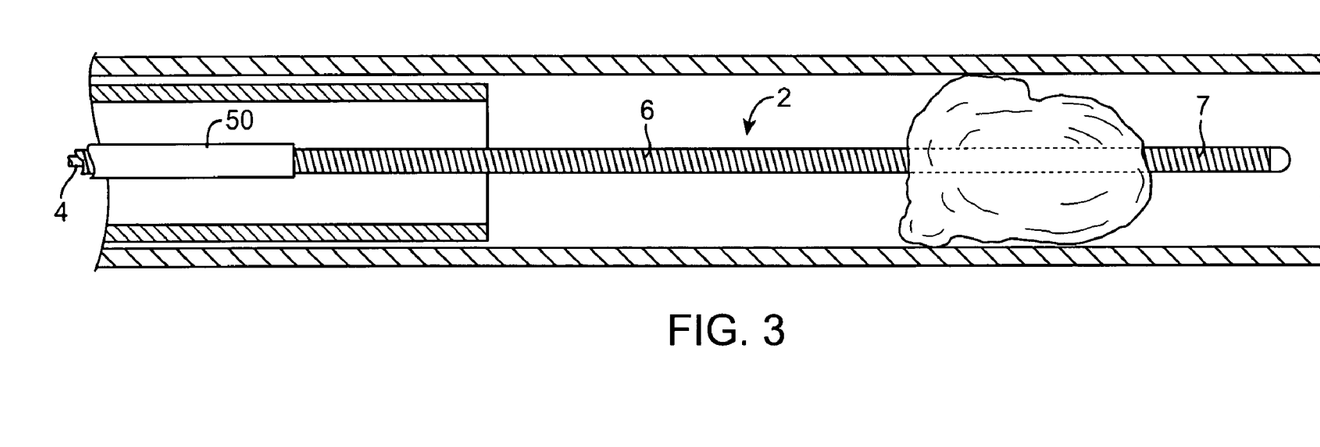
FIG. 3 shows the medical device passing through an obstruction.

The actuating element 6 may be an elongate element 11 such as a wire, tube, filament or the like. For example, the elongate element 11 may be a wire 9 which forms a coil 8 which is movable between stacked and relaxed positions. Referring specifically to FIG. 2, the stacked position is formed as the wire 9 forms a stacked coil which is produced by compressing the coil. The compressive force to stack the coil is applied by tensioning the main element 4 and/or applying compression to the actuating element 6. When the coil 8 is stacked, the windings of the coil are in intimate contact with one another. As will be described in greater detail below, the stacked shape is formed as opposing surfaces in the coil windings slide against one another until the stacked structure is formed. Some stacked conditions are quite stable, such as a substantially straight stacked position, and additional compressive force does not significantly alter the stacked shape. The stacked coil 8 of FIG. 2 has a substantially straight shape and, consequently, the coil 8 collapses the main element 4 into a substantially straight shape. The main element 4 may, of course, have some effect on the overall shape of the device 2 when the actuating element is in the stacked position but the shape is primarily determined by the stacked shape of the actuating element 6.

When the coil 8 is in the relaxed position of FIGS. 1 and 4, the actuating element 6 is much more flexible and the shape of the device 2 is primarily determined by the unbiased shape of the main element 4. The term "relaxed condition" as used herein does not necessarily mean completely unbiased and is used in reference to the stacked condition which has higher compressive force. Thus, the actuating element 6 may be under tension, in an unbiased state, or simply under less compression than the stacked condition. In fact, the difference in actuated and relaxed positions may be virtually imperceptible since even the smallest separation between the windings 10 will prevent the stacked condition. Thus, one advantage of the present invention is that little differential motion is required between the actuating element 6 and main element 4 to move between the relaxed and stacked conditions. The separation shown between the windings in the drawings is exaggerated for the purpose of clarifying the invention. The actuating element 6 may include a sleeve 10, such as a hypotube, attached to the coil as shown in FIGS. 1 and 2. Any structure, including pull wires, a collar or other suitable structure may be used instead of the sleeve 10 for manipulation of the actuating element 6 and main element 4.

Figure 5:
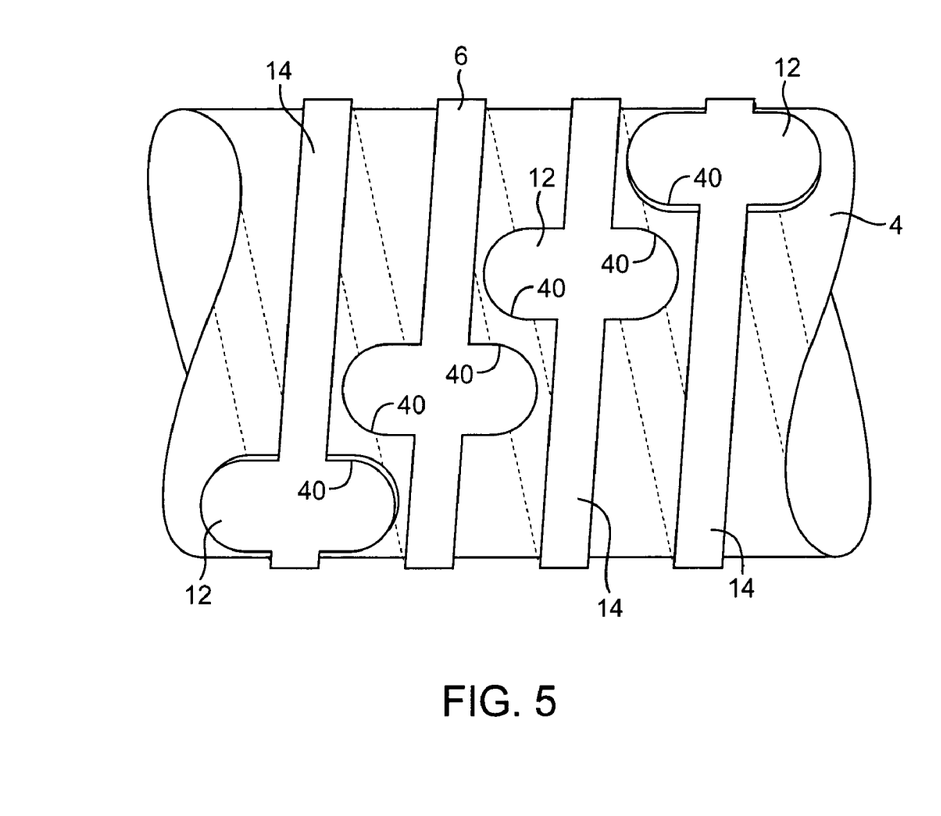
FIG. 5 shows another actuating element having varying thickness along its length.
Figure 6:
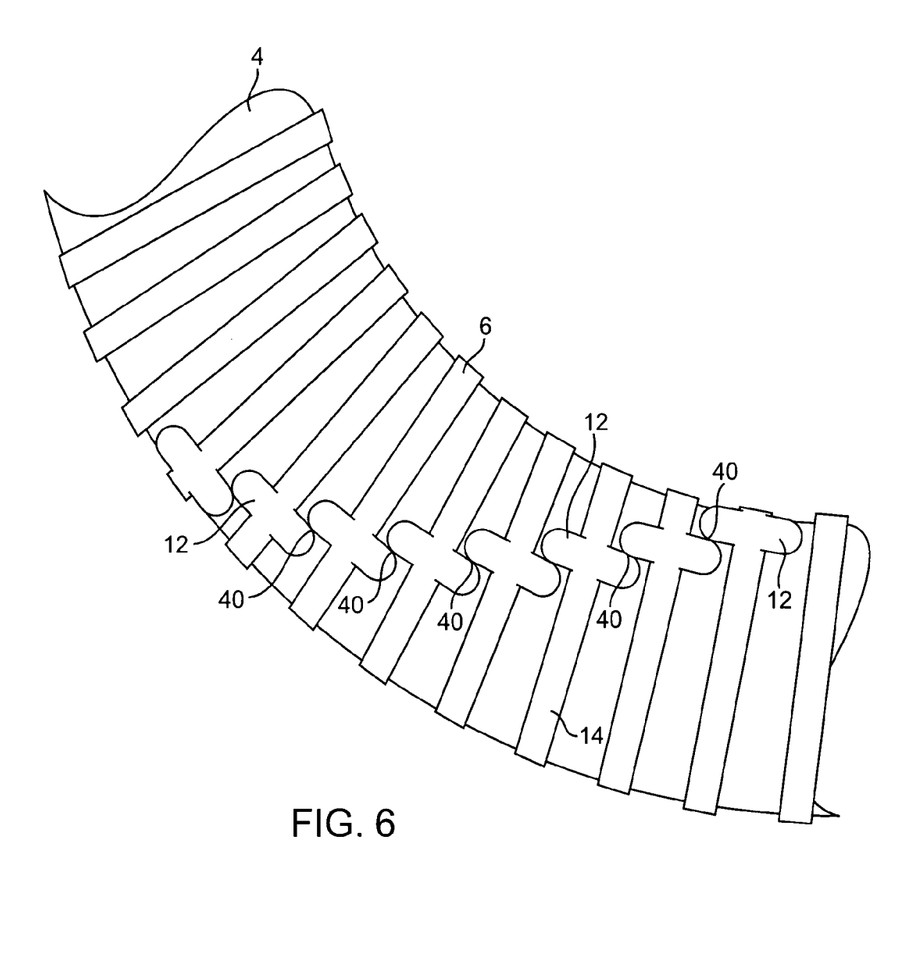
FIG. 6 shows the actuating element of FIG. 7 compressed to form a curved shape.

Referring to FIGS. 5 and 6, another actuating element 6 is shown which has a differing thickness along its length. When the actuating element 6 is wrapped around the main element 4 and compressed, the thicker regions 12 and thinner regions 14 align with one another as shown in FIG. 6 to shape the main element 4 with the thinner regions 14 being on the radially inner side and the thicker regions 12 on the radially outer side. In this manner, the element 6 can be used to provide curved shapes such as helical.

Figure 7:
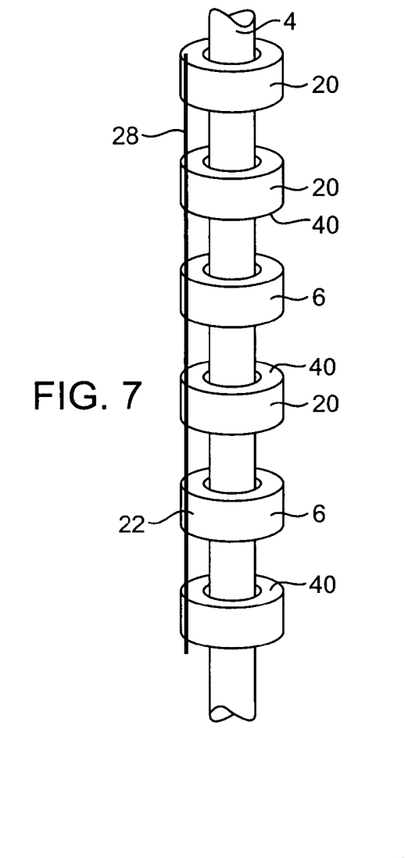
FIG. 7 shows a main element having a number of independent elements slidable on the main element.
Figure 8:
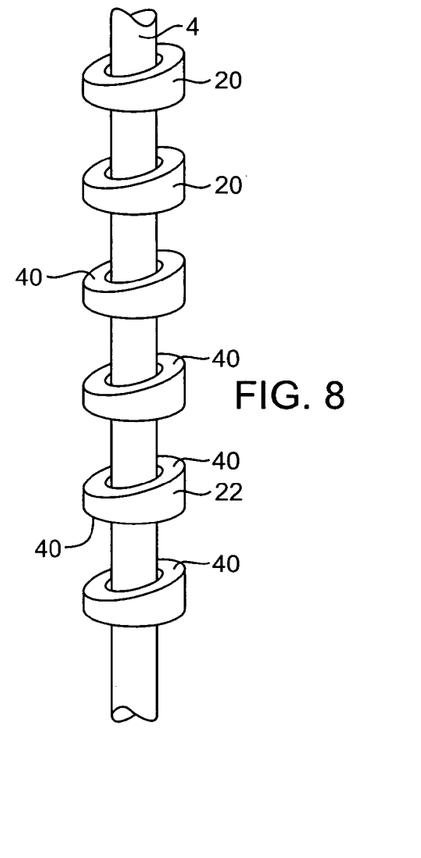
FIG. 8 shows a non-circular main element which maintains the orientation of the actuating element.
Figure 9:
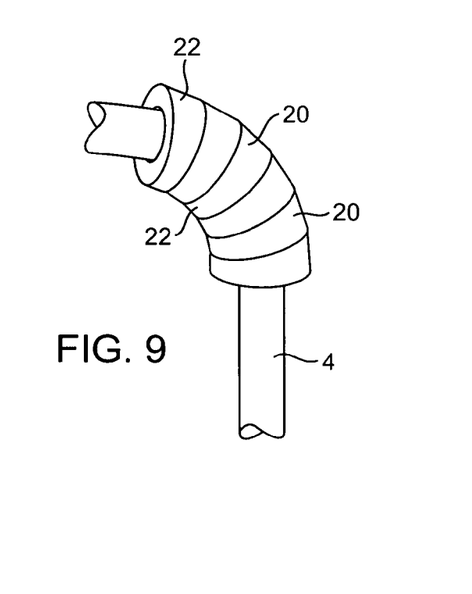
FIG. 9 shows the elements of FIG. 8 compressed to curve the main element.

Referring to FIGS. 7–9, the actuating element 6 may include a number of independent elements 20 rather than a continuous element. For example, the actuating element may have a number of rings 22 which, when stacked, form a predetermined shape. For example, the rings 22 may simply form a substantially straight configuration similar to the stacked coil. The independent elements 20 may also form a predetermined shape, such as curved, when stacked. The elements 20 may have a member 28 which couples the elements 20 together to help maintain the angular orientation of the elements 20 on the main element 4. Alternatively, the main element 4 may have a non-circular cross-section, such as oval, which interacts with the elements 20 so that the elements 20 maintain their angular orientation with respect to the main element 4 and to one another as shown in FIGS. 8 and 9.

Figure 10:
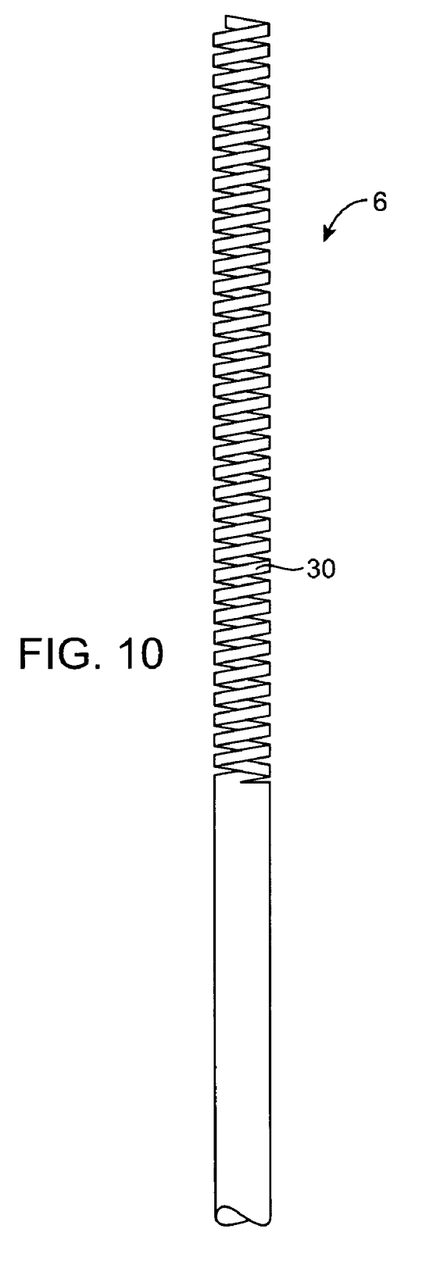
FIG. 10 shows a tube cut helically.
Figure 11:
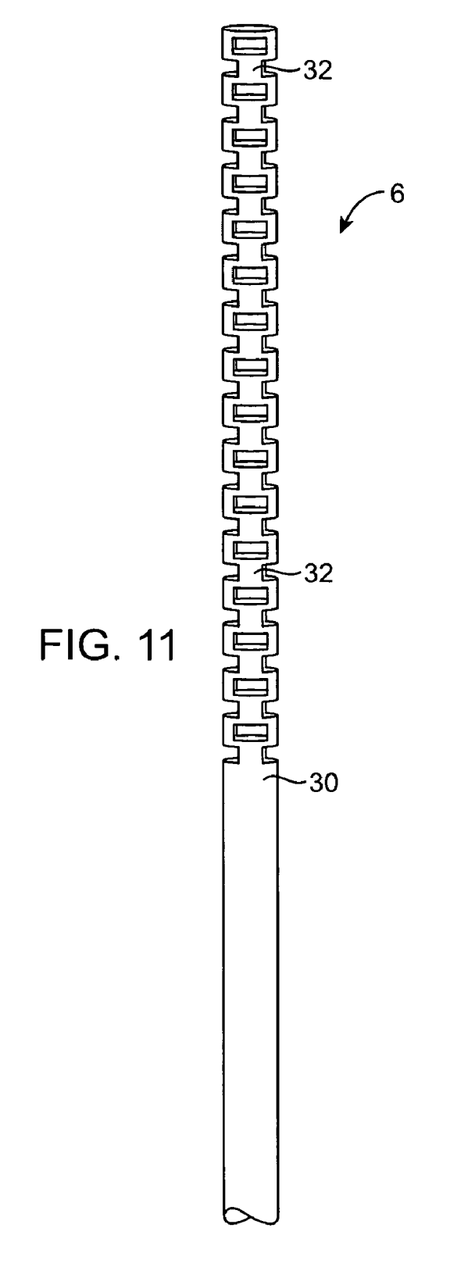
FIG. 11 shows a tube having slots therein.

Referring to FIGS. 10 and 11, the actuating element 6 may also be formed from a tube 30. The tube 30 may be cut helically or slotted. When the actuating element 6 is compressed, the cut sections of the tube 30 stack together to curve the main element (not shown) with a longitudinal rib 32 extending along a radially outer side. The tube 30 may be used to form relatively complicated shapes by first shaping the tube 30 into the desired shape and then cutting the tube helically, into individual rings or sections, or in some other suitable manner. The cut tube or parts of the tube are then mounted to a non-circular main element 4 so that the tube again forms the desired shape when compressed and stacked.

A number of aspects of the present invention rely on forces developed during stacking of the actuating element 6 to change the shape of the main element 4. Referring again to FIGS. 1 and 5–8, the actuating element 6 has a plurality of opposing surfaces 40 along its length. The opposing surfaces 40 slide against one another as compressive force is exerted on the actuating element 6. The opposing surfaces 40 continue to slide against one another until the stacked position is achieved. For example, each winding 42 of the coil in FIGS. 1 and 2 essentially forms opposing surfaces 40 with each of the adjacent windings. The individual elements in FIGS. 7–9 also form the opposing surfaces 40 on each side which interact with surfaces 40 on the adjacent elements. The present invention provides numerous opposing surfaces which act together to apply forces to the main element. In one aspect of the present invention, the actuating element preferably has at least 100 opposing surfaces per inch of the main element or even at least 200 opposing surfaces per inch of the main element. When using a 0.005 inch diameter wire, for example, as the actuating element, the wire will essentially form about 200 opposing pairs per linear inch of actuating element.

One advantage of the present invention is that the actuating element 6 can be made quite small. For example, an elongate element, such as a wire, having a diameter of 0.003 inch can be used to form the actuating element 6. Although the actuating element 6 is small and flexible, the actuating element 6 can exert relatively high forces on the main element due to the forces developed during stacking. Stated another way, the actuating element may have a thickness of no more than 0.015 inch, no more than 0.005 inch or even no more than 0.003 inch where the thickness is measured along the length of the main element 4. The main element 4 itself may have any suitable size depending upon the particular application but is generally much stiffer than the actuating element 6. For example, the main element 4 may be a wire having a size of greater than 0.030 inch or stated another way has a size of 0.025 to 0.125 inch. The actuating element 6 is wrapped around the main element with very little or essentially no spacing between the windings so that very little differential movement is required to achieve the stacked condition as mentioned above. As mentioned above, very little spacing is required between the windings to prevents the stacked condition and, conversely, very little motion may be required to achieve the stacked condition.

An advantage of using the stacking phenomenon is that relatively high forces can be imparted along the entire length of the main element, rather than a few locations, using a relatively thin, flexible element. When the actuating element is in the relaxed condition, the small size of the actuating element does not significantly affect the physical characteristics, such as flexibility, of the main element. In this manner, the device provides the ability to advance relatively robust devices through catheters without the device binding since the actuating element can keep relatively stiff, robust devices in a relatively straight configuration during advancement. For example, the device of FIGS. 1 and 2 may be somewhat difficult to advance through a catheter, particularly when a stiff wire is used, since the catheter can bind up within the delivery catheter during advancement. The present invention provides the ability to collapse the device during advancement through the catheter so that the device does not bind within the catheter.

Another advantage in a few aspects of the present invention is that the device assumes the desired physical geometry and characteristics when the actuating element is relaxed yet the device can be collapsed easily with little relative motion and with a very thin, flexible filament or wire which does not significantly impact the main elements physical characteristics when relaxed.

In one specific application of the present invention, the device can be used to access areas which usually require a delivery catheter such as a microcatheter 50. Many filters, obstruction removal devices and other vascular devices are naturally biased to their expanded condition. Thus, when advancing these devices through a blood vessel, the devices are generally held in a delivery catheter, such as a microcatheter, for advancement into or through a troublesome region such as an obstruction, stenosis, AVM, vasospasm, aneurysm or smalldiameter or tortuous vasculature.

Figure 12:
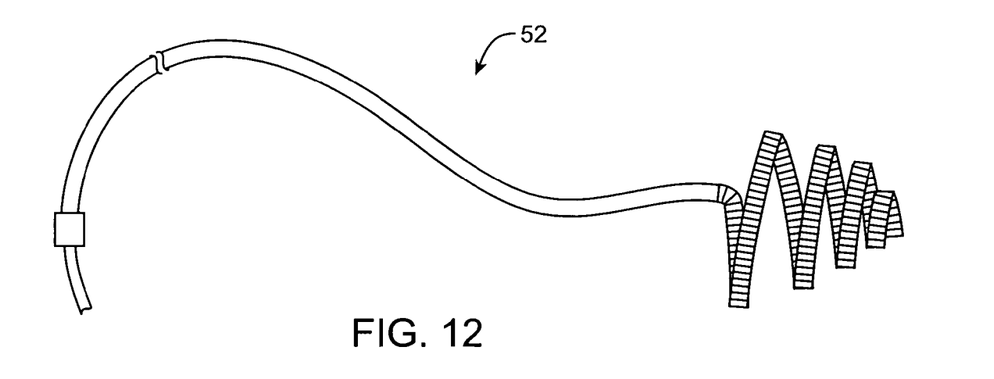
FIG. 12 shows a filter in accordance with the present invention.
Figure 13:
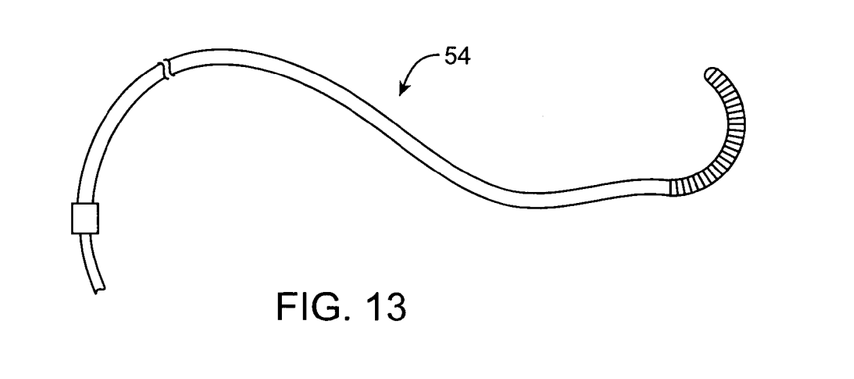
FIG. 13 shows a guidewire in accordance with the present invention.

The present device can be used without a delivery catheter as is required with many self-expanding medical devices. Referring again to FIGS. 3 and 4, for example, the device 2 can be collapsed and then advanced through an obstruction or small or tortuous regions by itself. At that desired location and at the desired time, the device 2 may be deployed to perform a procedure which may be any suitable procedure including those described or mentioned herein. Placing a catheter through such an obstruction or narrowed region may increase the potential to dislodge part of the obstruction or arterial plaque. Thus, the present invention may be formed as a filter 52 (FIG. 12) or simply as a guidewire 54 (FIG. 13) which can be moved between the two conditions as described in any manner herein for moving the devices between two positions such as expanded and collapsed or curved and substantially straightened. The soft tip, which is provided by the distal portion of the coil, also helps the devices described herein pass through blood vessels and, in particular, troublesome regions in a manner similar to a guidewire.

Figure 14:
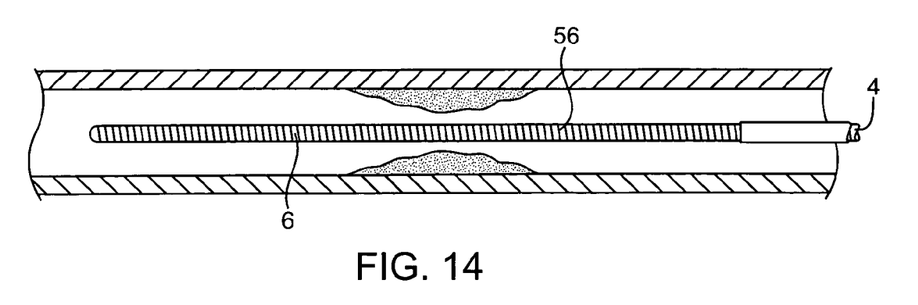
FIG. 14 shows a medical device passing through a narrowed region of a blood vessel.
Figure 15:
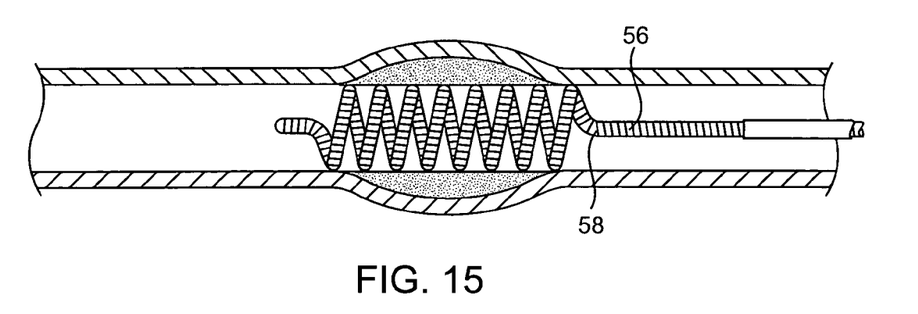
FIG. 15 shows the medical device expanded in the blood vessel.
Figure 16:
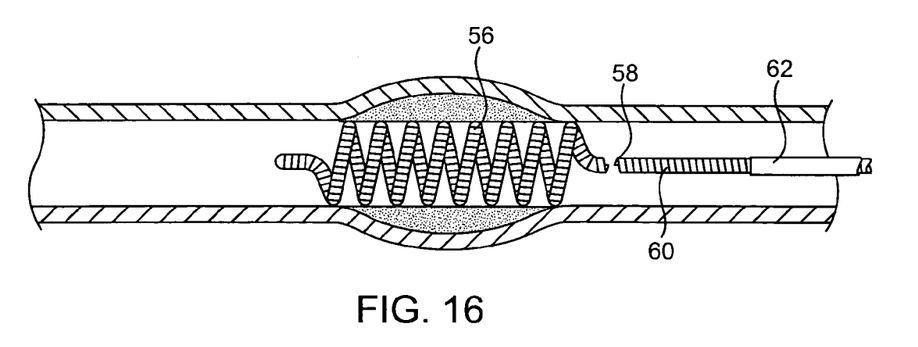
FIG. 16 shows the medical device deployed within the blood vessel.

Referring to FIGS. 14–16, a device 56 may also be introduced into a vessel to temporarily or permanently treat the vessel. The medical device 56 may be used to open a vessel in a manner similar to a stent or to treat vasospasm. The medical device 56 may be released as shown in FIG. 16 or may be temporarily deployed and then removed. For example, the medical device 56 may have a severable bond 58 which permits release of the device. Any suitable bond may be used including a mechanical and/or electrolytically severable bond. For example, the main element 4 may have an electrolytically severable bond and the actuating element 6 may have a discontinuity along the coil 60 or at the coil to sheath 62 interface which permits separation of the actuating element when the main element 4 is released.

The present invention has been described with reference to various preferred embodiments, however, it should be understood that the present invention may be used in many other medical devices not mentioned herein.

What is claimed is:

1. A method of changing the shape of a medical device in a patient, comprising the steps of:
   providing a medical device having a main element and an actuating element, the actuating element being movable between a stacked position and a relaxed position, the actuating element moving from the relaxed position to the stacked position upon application of a compressive force to the actuating element, the main element being deformed from a first position to a second position by the actuating element as the actuating element moves to the stacked position, the actuating element being a coil wrapped around the main element;
   introducing the medical device into a patient;
   moving the actuating element between the stacked and relaxed positions thereby moving the actuating element between the first and second positions.

2. The method of claim 1, wherein:
   the providing step is carried out with the actuating element having a plurality of opposing surfaces, the plurality of opposing surfaces being longitudinally spaced along the main element, the plurality of opposing surfaces sliding against one another when moving from the relaxed position toward the stacked position.

3. The method of claim 1, wherein:
   the providing step is carried out with the opposing surfaces sliding against one another until the stacked shape is formed, wherein an increase in compressive force after the stacked shape is formed does not substantially change the shape of the main element.

4. The method of claim 1, wherein:
   the providing step is carried out with the main element being a wire.

5. The method of claim 1, wherein:
   the providing step is carried out with the coil having a varying thickness, wherein the stacked position of the coil aligns segments having relatively smaller thickness and segments having relatively larger thickness.

6. The method of claim 5, wherein:
the using step is carried out with the procedure being a procedure selected from the group consisting of cardiac, vascular, tracheobronchial, gastrointestinal, urological and contraceptive.

7. The method of claim 1, wherein:
the providing step is carried out with the coil being stacked when in the compressed position.

8. The method of claim 1, wherein:
the coil is wound around the main element at an angle of 60 to 90 degrees relative to a longitudinal axis of the main element.

9. The method of claim 1, further comprising the step of:
using the medical device to perform a procedure in the patient.

10. The method of claim 1, wherein:
the providing step is carried out with the main element being non-circular and the actuating element being mounted around and slidable on the main element, the main element maintaining an angular orientation of the actuating element with respect to the main element.

11. The method of claim 10, wherein:
the delivering step is carried out with the device being advanced through a blood vessel, the device being advanced through the blood vessel with the actuating element in the stacked position thereby holding the main element in the collapsed position, the device being advanced by itself through the narrowed region without use of a delivery catheter.

12. The method of claim 1, further comprising the step of:
separating at least part of the main element from the medical device and leaving the separated part of the main element in the patient.

13. The method of claim 1, wherein:
the providing step is carried out with the actuating element being a hypotube.

14. The method of claim 13, wherein:
the providing step is carried out with the hypotube being cut helically.

15. The method of claim 1, wherein:
the providing step is carried out with the main element being in an expanded shape when in the first position; and
the moving step is carried out so that the main element moves the main element to a collapsed condition as the actuating element moves to the stacked position.

16. The method of claim 1, wherein:
the providing step is carried out with the actuating element extending around the main element.

17. The method of claim 1, wherein:
the providing step is carried out with the actuating element being a coil, wherein the coil is a substantially stacked coil when in the stacked condition.

18. The method of claim 1, wherein:
the providing step is carried out with the main element being flexible when in the unbiased position; and
the moving step is carried out to expand the main element toward the stacked position.

19. A method of changing the shape of a medical device in a patient, comprising the steps of:
providing a medical device having a main element and an actuating element, the actuating element being movable between a stacked position and a relaxed position, the actuating element moving from the relaxed position to the stacked position upon application of a compressive force to the actuating element, the main element being deformed from a first position to a second position by the actuating element as the actuating element moves to the stacked position, the actuating element having a number of independent elements each having a throughhole through which the main element extends;
introducing the medical device into a patient;
moving the actuating element between the stacked and relaxed positions thereby moving the actuating element between the first and second positions.

* * * * *